(12) United States Patent
Nakagawa et al.

(10) Patent No.: US 11,826,076 B2
(45) Date of Patent: Nov. 28, 2023

(54) MEDICAL NEEDLE WITH PROTECTOR

(71) Applicant: KABUSHIKI KAISHA TOP, Tokyo (JP)

(72) Inventors: Daisuke Nakagawa, Tokyo (JP); Sho Takayanagi, Tokyo (JP); Dai Takahashi, Tokyo (JP)

(73) Assignee: KABUSHIKI KAISHA TOP, Tokyo (JP)

( * ) Notice: Subject to any disclaimer, the term of this patent is extended or adjusted under 35 U.S.C. 154(b) by 235 days.

(21) Appl. No.: 17/242,817

(22) Filed: Apr. 28, 2021

(65) Prior Publication Data

US 2021/0244440 A1 Aug. 12, 2021

Related U.S. Application Data

(63) Continuation of application No. 16/094,516, filed as application No. PCT/JP2017/011042 on Mar. 17, 2017, now Pat. No. 11,026,721.

(30) Foreign Application Priority Data

Apr. 26, 2016 (JP) .................................. 2016-088440

(51) Int. Cl.
*A61B 17/34* (2006.01)
*A61M 5/158* (2006.01)
*A61M 5/32* (2006.01)

(52) U.S. Cl.
CPC ......... *A61B 17/3496* (2013.01); *A61M 5/158* (2013.01); *A61M 5/32* (2013.01); *A61B 2017/347* (2013.01); *A61B 2017/3492* (2013.01)

(58) Field of Classification Search
CPC .......... A61B 17/3496; A61B 2017/347; A61B 2017/3492; A61M 5/32; A61M 5/158; A61M 5/1626; A61M 5/3293
See application file for complete search history.

(56) References Cited

U.S. PATENT DOCUMENTS

| 4,832,696 A | 5/1989 | Luther |
| 5,928,199 A | 7/1999 | Nakagami |

(Continued)

FOREIGN PATENT DOCUMENTS

| JP | 07-075671 | 3/1995 |
| JP | 07-204267 | 8/1995 |

(Continued)

OTHER PUBLICATIONS

International Search Report, dated Jun. 6, 2017 (Jun. 6, 2017), 2 pages.

(Continued)

*Primary Examiner* — Julian W Woo
(74) *Attorney, Agent, or Firm* — Rankin, Hill & Clark LLP

(57) ABSTRACT

There is provided a medical needle with a protector that allows separately molded hub and protector to be easily assembled together. A medical needle with a protector (1) includes: a hub (3) that supports a needle tube (2); a protector (4) capable of storing the needle tube (2); a first lock unit (42a, 42b, 73) that locks the hub (3) to the protector (4) capable of unlocking in a first state; and a second lock unit (43, 75) that locks the hub (3) to the protector (4) incapable of a transition to the first state in a second state. The protector includes a large cylindrical portion (41), a protrusion piece (43), and a width-increased portion (42). The width-increased portion (42) is provided on the outer peripheral side of the protrusion piece (43) and has a minor axis and a major axis. The protrusion piece (43) is formed integrally with the large cylindrical portion (41) on the major axis side of the width-increased portion (42).

7 Claims, 8 Drawing Sheets

(56) References Cited

U.S. PATENT DOCUMENTS

| | | |
|---|---|---|
| 8,900,199 B2 | 12/2014 | Kawai |
| 9,585,610 B2 | 3/2017 | Terasawa |
| 10,314,984 B2 | 6/2019 | Koehler |
| 2006/0135910 A1 | 6/2006 | Luther et al. |

FOREIGN PATENT DOCUMENTS

| | | |
|---|---|---|
| JP | 3134920 | 2/2001 |
| JP | 2008-029812 | 2/2008 |
| JP | 2010-187984 | 9/2010 |
| JP | 2010-214096 | 9/2010 |
| JP | 2013-192738 | 9/2013 |
| JP | 2017-196060 | 11/2017 |

OTHER PUBLICATIONS

Japanese Office Action dated Oct. 1, 2019, from corresponding application JP 2019-165658, 4 pages.
Japanese Office Action dated Oct. 1, 2019, from corresponding application JP 2019-165659, 6 pages.
Japanese Office Action dated Oct. 1, 2019, from corresponding application JP 2019-165660, 4 pages.
Japanese Office Action dated Oct. 1, 2019, from corresponding application JP 2019-165661, 4 pages.

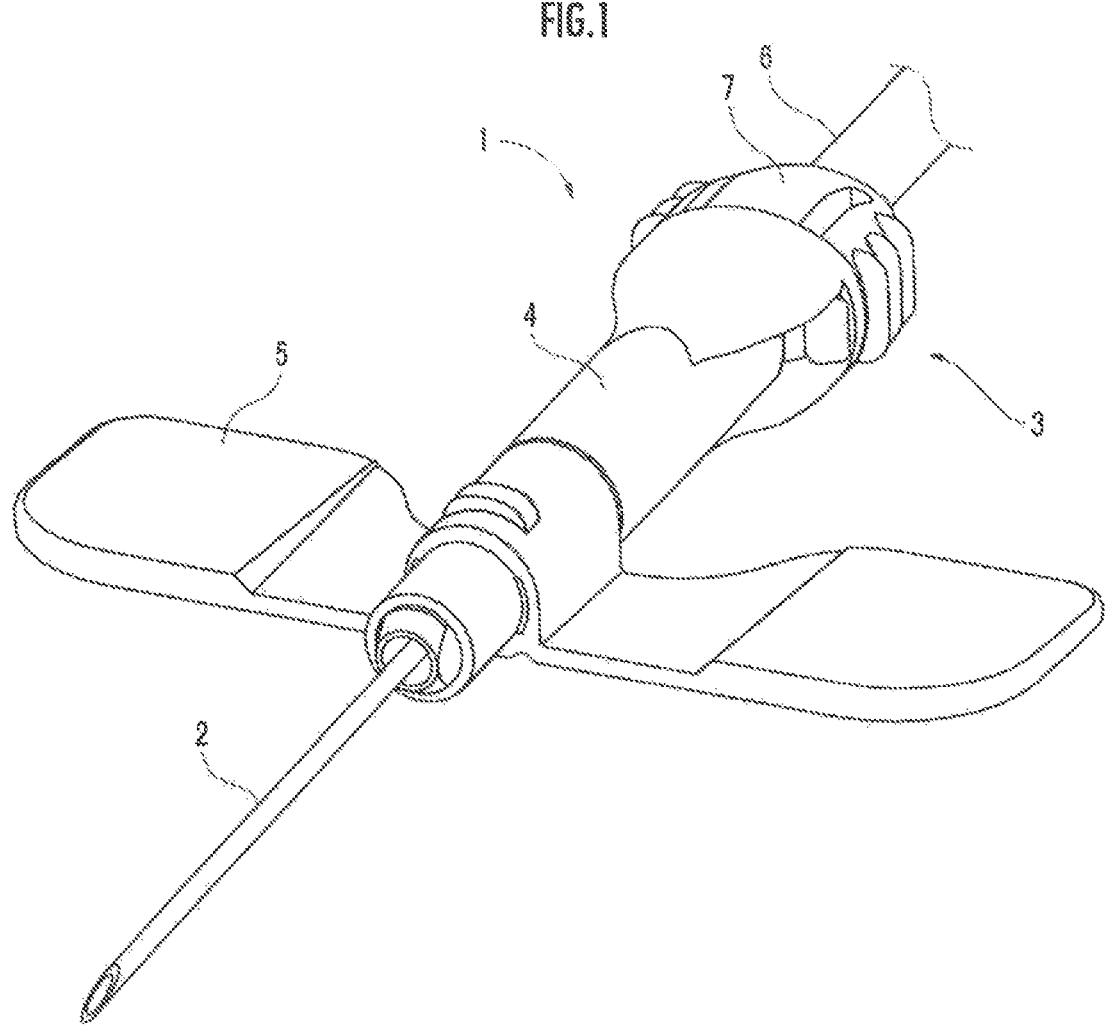

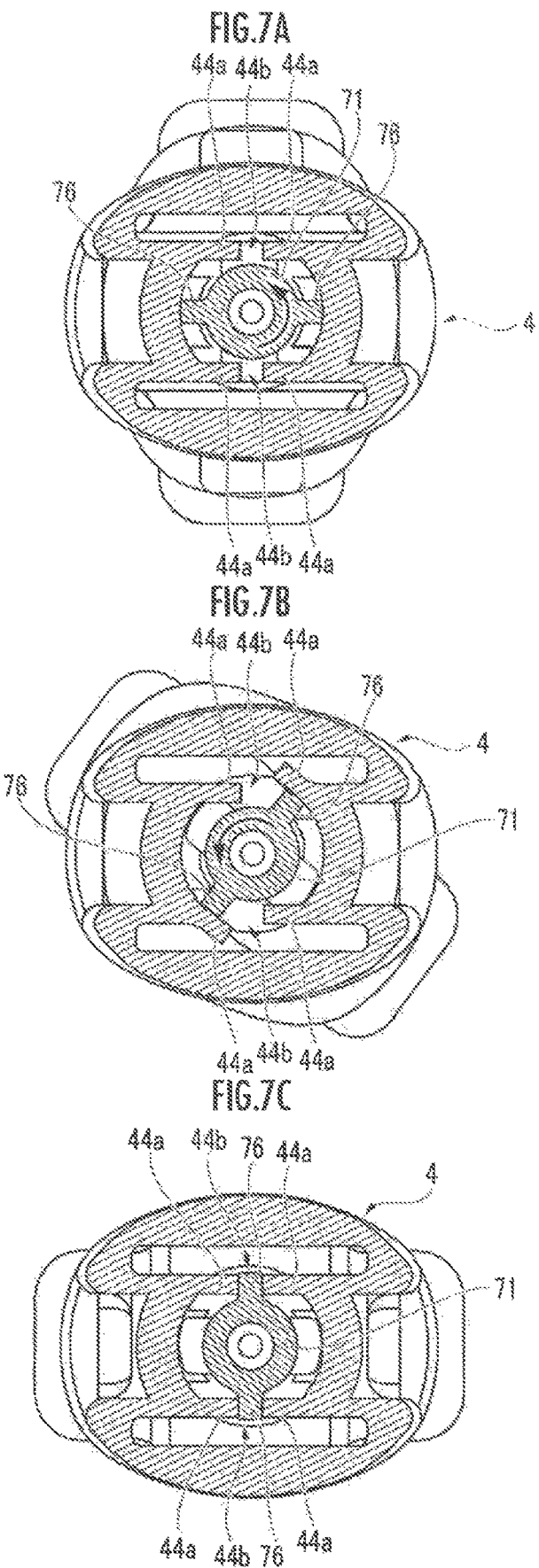

MEDICAL NEEDLE WITH PROTECTOR

TECHNICAL FIELD

The present invention relates to a medical needle with a protector.

BACKGROUND ART

There has been conventionally known a medical needle with a protector that has a hub with a front end supporting the rear end of a needle tube and a rear end connected to a flexible tube and a cylindrical protector capable of storing the hub (for example, refer to Patent Literature 1).

In the medical needle with a protector, it is desired that, after insertion into a blood vessel or the like, the needle tube does not come off, and after use, the needle tube housed in a needle protector does not protrude again to avoid erroneous puncture. Thus, the medical needle with a protector includes: a first lock unit that locks the hub to the protector in a manner capable of unlocking with the needle tube protruded from the protector; and a second lock unit that locks the hub to the protector in a manner incapable of unlocking with the needle tube stored in the protector.

According to the medical needle with a protector, when the needle tube is protruded from the protector and is inserted into a blood vessel or the like, the hub is locked in the protector by the first lock unit to prevent the needle tube from coming off the blood vessel. After use, the hub is unlocked from the first lock unit so that the needle tube can be stored in the protector.

Further, according to the medical needle with a protector, when the needle tube is stored in the protector, the hub is locked to the protector by the second lock unit and thus will not protrude again, thereby capable of preventing erroneous puncture.

CITATION LIST

Patent Literature

Patent Literature 1: JP 3134920 B2

SUMMARY OF INVENTION

Technical Problem

In the foregoing conventional medical needle with a protector, each of the hub and the protector are made of a synthetic resin and formed by injection molding. However, when an attempt is made to assemble the separately molded hub and protector together, there is a problem the first lock unit or the second lock unit may interfere, and cannot assemble.

To solve the foregoing problem, for example, it is considered that either one of the hub and the protector may be molded in advance and is placed in advance in a molding die at the injection molding of the other for insert molding so that the product with the hub and the protector assembled together can be obtained.

However, the insert molding requires a molding die of an intricate structure which would cause the inconvenience of performing complicated operations.

To eliminate such inconvenience, an object of the present invention is to provide a medical needle with a protector that allows the separately molded hub and protector to be easily assembled together.

Solution to Problem

To attain the object, a medical needle with a protector of the present invention includes: a hub at a front end supporting a rear end of a needle tube; a cylindrical protector that is capable of storing the needle tube by sliding the hub; a first lock unit that locks the hub to the protector in a manner capable of unlocking in a first state that the needle tube protruded from the protector; and a second lock unit that locks the hub to the protector in a manner incapable of at least a transition to the first state in a second state that the needle tube stored in the protector. A front end side part of the hub includes a step shape that forms an end surface facing to the front end side by separating at least a part of outer peripheral surface in a direction away from an axial line of the hub. The protector includes: a large cylindrical portion extending in a needle axis direction; a protrusion piece that is provided on a rear end side of the large cylindrical portion, extends to a rear end side of the protector, and is elastically deformable in a direction away from an axial line of the protector; a width-increased portion that is provided on an outer peripheral side of the protrusion piece on the rear end side of the large cylindrical portion, has a larger diameter than the large cylindrical portion, and has a minor axis and a major axis when viewed along the needle axis direction. The second lock unit is configured such that a rear end side of the protrusion piece contacts with the end surface of the step shape in the second state. The protrusion piece is formed integrally with the large cylindrical portion on the major axis side of the width-increased portion.

In the medical needle with the protector of the present invention, it is preferred that the protrusion piece has a surface inclined to the axial line of the protector on a side of the axial line of the protector.

In the medical needle with the protector of the present invention, it is preferred that the first lock unit is configured such that, a window provided on the major axis side of the width-increased portion is locked to the hub, and the window is provided to open the outer peripheral side of at least a part of the protrusion piece.

In the medical needle with the protector of the present invention, it is preferred that the hub includes a connection tube portion connected to a flexible tube, the first lock unit is configured such that, a window provided on the major axis side of the width-increased portion is locked to an arm provided on the hub, and at least a part of the connection tube portion is located on a rear end side from a rear end of a part along a length of the hub with a space from the hub of the arm.

In the medical needle with the protector of the present invention, it is preferred that the protector includes a recessed portion provided on the minor axis side of the width-increased portion.

In the medical needle with the protector of the present invention, it is preferred that the hub includes a needle tube support portion supporting the needle tube, a connection tube portion connected to a flexible tube, and a hollow portion connecting the needle tube support portion and the connection tube portion.

In the medical needle with the protector of the present invention, it is preferred that the protector has a wing-like member extending to the major axis side of the width-increased portion.

The medical needle with the protector according to another aspect of the present invention includes: a hub at a front end supporting a rear end of a needle tube; a cylindrical protector that is capable of storing the needle tube by sliding the hub; a first lock unit that locks the hub to the protector in a manner capable of unlocking with the needle tube protruded from the protector; and a second lock unit that locks the hub to the protector in a manner incapable of unlocking with the needle tube stored in the protector. A front end of the hub includes: a pair of first protrusion portions that is provided on a first axial line orthogonal to an axial line of the hub and is individually protruded in a direction away from an outer peripheral surface of the hub; and a pair of second protrusion portions that is orthogonal to the axial line of the hub at a first predetermined space from the first protrusion portions to the rear end side, is provided on a second axial line crossing the first axial line at a predetermined angle as seen from the axial line of the hub. A rear end of the protector has: a pair of protrusion pieces that is provided on a third axial line orthogonal to an axial line of the protector, extends individually from an inner peripheral surface of the protector toward the axial line of the protector while inclining toward the rear end side, and is elastically deformable in a direction away from the axial line of the protector; and a pair of side wall portions that is provided on the inner peripheral surface of the protector with a second predetermined space equal to or smaller than the first predetermined space from the protrusion pieces of the protector to the front end side and is opposed to each other on a fourth axial line crossing the third axial line at the predetermined angle as seen from the axial line of the protector. The second lock unit is configured such that, when the needle tube is stored in the protector, front end sides of the side wall portions of the protector are locked to the first protrusion portions of the hub and rear end sides of the protrusion pieces of the protector are locked to the second protrusion portions. A space between the pair of side wall portions is set to be equal to or larger than a maximum width of the both protrusion portions in the direction orthogonal to the first axial line as seen from the axial line of the hub and smaller than a distance from one protrusion end to the other protrusion end of each of the protrusion portions.

The medical needle with the protector according to another aspect of the present invention includes the hub and the cylindrical protector into which the hub is to be assembled. The hub has the front end supporting the rear end of the needle tube, and the protector stores the needle tube.

When the medical needle with a protector according to another aspect of the present invention is inserted into a blood vessel or the like with the needle tube protruded from the protector, the hub is locked in the protector by the first lock unit to prevent the needle tube from coming off the blood vessel or the like.

In the medical needle with the protector according to another aspect of the present invention, after removal from the blood vessel or the like, the hub is released from the state of being locked in the protector by the first lock unit and the hub is moved backward to draw the needle tube into the protector.

Then, when the first protrusion portions and the second protrusion portions of the hub are moved backward to the rear end side of the protector, since the protrusion pieces at the rear end side of the protector extend from the inner peripheral surface of the protector to the rear end side toward the axial line of the protector, the first protrusion portions and the second protrusion portions are deformed in the direction away from the axial line of the protector by the rear end sides of the second protrusion portions. When the hub is further relatively moved backward, the protrusion pieces go beyond the second protrusion portions and return to the original state due to their elasticity. Accordingly, the protrusion pieces are locked from the rear end side by the second protrusion portions.

At this time, the first predetermined space between the first protrusion portions and the second protrusion portions of the hub is equal to or larger than the second predetermined space between the protrusion pieces and the side wall portions of the protector, and thus the first protrusion portions of the hub lock the side wall portions of the protector.

As a result, the first protrusion portions and the second protrusion portions of the hub constituting the second lock unit sandwich the side wall portions and the protrusion pieces of the protector. Accordingly, the hub is locked in the protector in a manner incapable of unlocking and cannot be moved forward or backward. Therefore, the needle tube will not be protruded again from the protector, which makes it possible to prevent wrong insertion.

To assemble the hub into the protector, the front end side of the hub is inserted into the rear end side of the protector. At this time, when an attempt is made to insert the front end side of the hub into the rear end side in the posture in which the hub is stored in the protector, the space between the side wall portions is set to be smaller than the distance from the one protrusion end to the other protrusion end of each of the first protrusion portions, and thus the first protrusion portions hit against the side wall portions to inhibit the insertion.

However, the space between the side wall portions is equal to or larger than the maximum width of the first protrusion portions in the direction orthogonal to the first axial line as seen from the axial line of the hub. Accordingly, rotating the protector and the hub relatively around their central axes makes it possible to insert the hub from the side wall portions to the front end side while avoiding a collision with the side wall portions.

The second protrusion portions can be moved forward by the rotation while avoiding a collision with the protrusion pieces, but the space between the side wall portions is set to be smaller than the distance from the one protrusion end to the other protrusion end of each of the second protrusion portions, and thus the hub hits against the side wall portions and cannot be inserted any longer.

However, the space between the side wall portions is equal to or larger than the maximum width of the second protrusion portions in the direction orthogonal to the first axial line as seen from the axial line of the hub. Accordingly, rotating the protector and the hub in the direction opposite to the previous direction makes it possible to insert the second protrusion portions from the side wall portions to the front end side while avoiding a collision with the side wall portions, whereby the hub is completely assembled into the protector.

Therefore, according to the medical needle with a protector according to another aspect of the present invention, the separately molded hub and protector can be easily assembled together without performing insert molding or the like.

In the medical needle with the protector according to another aspect of the present invention, it is preferred that the outer peripheral surface of the hub has a streak along the axial line of the hub and the side wall portions have a slit through which the streak passes.

According to this, when the hub is relatively moved backward from the protector, the streak in the hub is guided by the slit in the side wall portions along the axial line of the hub. Accordingly, the hub can be smoothly moved backward.

In the medical needle with the protector according to another aspect of the present invention, it is preferred that the side wall portions are formed from a pair of plate spring members elastically deformable in a direction in which the side wall portions of the protector are separated from the axial line of the protector, and the slit is formed by separating the opposing protrusion ends of the plate spring members from each other at a predetermined distance.

According to this, when the protector and the hub are gradually rotated in the direction opposite to the previous direction in a relative manner around their central axes, the streak deforms the plate spring members outward. Then, when the protector and the hub further rotate, the plate spring members go over the streak and return to the original state due to their elasticity. Accordingly, the streak is fitted into the slit formed by the gap between the pair of plate spring members. Therefore, according to the thus configured medical needle with a protector, the hub with the streak can be easily assembled with the protector.

The protector preferably includes a pair of wing-like members. In the medical needle with a protector according to another aspect of the present invention, the needle tube can be inserted into a blood vessel or the like by overlapping and picking up the pair of wing-like members. In the medical needle with a protector according to another aspect of the present invention, after the insertion of the needle tube into the blood vessel or the like, the pair of wing-like members can be opened and fixed to the skin by an adhesive tape or the like.

BRIEF DESCRIPTION OF DRAWINGS

FIG. 1 is a perspective view of a configuration of a medical needle with a protector according to an embodiment.

FIG. 2A is a perspective view, FIG. 2B is a vertical cross-sectional view with respect to an axial direction, and FIG. 2C is a horizontal cross-sectional view.

FIG. 3A is a perspective rear view, FIG. 3B is a horizontal cross-sectional view, and FIG. 3C is a vertical cross-sectional view with respect to the axial direction.

FIGS. 7A, 7B and 7C are cross-sectional views of FIG. 6B taken along line VII-VII in which the protector and the hub are relatively rotated 90° in opposite directions around their central axes. FIG. 7A is a cross-sectional view before the reverse rotation, FIG. 7B is a cross-sectional view in the course of the rotation, and FIG. 7C is a cross-sectional view after completion of the rotation.

FIG. 8A is a perspective view of a hub according to the modification example; FIG. 8B is a horizontal cross-sectional view of a protector according to the modification example; and FIG. 8C is an enlarged perspective view of a front end of the modification example.

DESCRIPTION OF EMBODIMENT

Figure 2A:
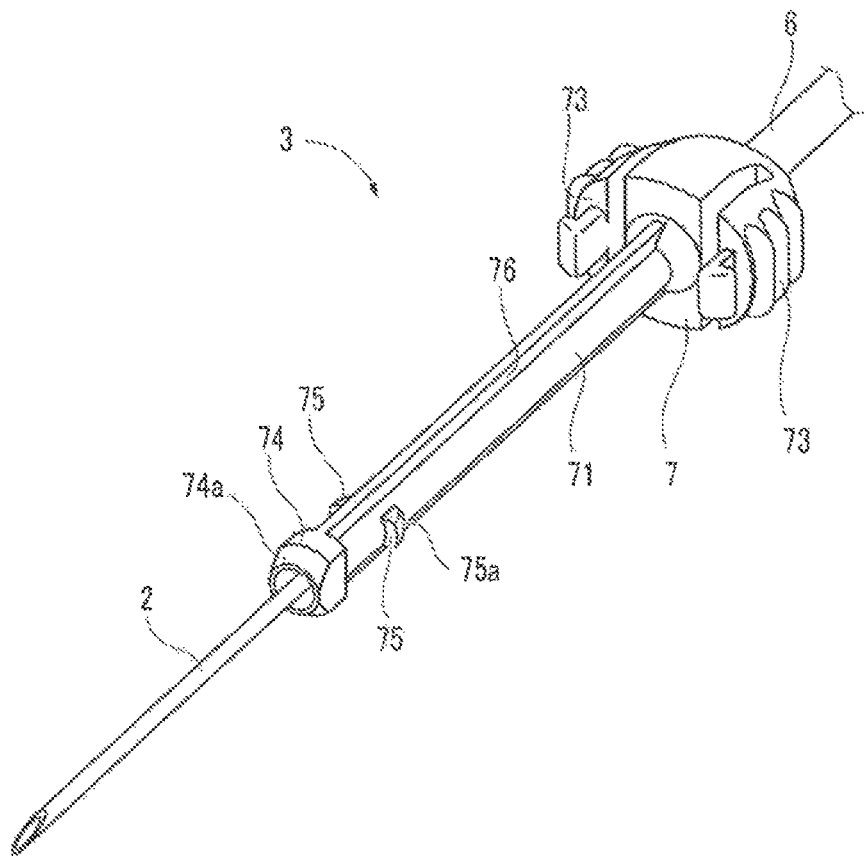
FIG. 2A, FIG. 2B and FIG. 2C are illustrative diagrams of a hub illustrated in FIG. 1.

Next, an embodiment of the present invention will be described in detail with reference to the accompanying drawings.

As illustrated in FIG. 1, a medical needle with a protector 1 of the present embodiment includes a hub 3 that supports a needle tube 2 with a sharpened front end, a cylindrical protector 4 into which the hub 3 is assembled, and a pair of wing-like members 5 externally fitted to the protector 4.

The protector 4 is formed by injection molding of a polypropylene resin or the like and is capable of storing the needle tube 2. The wing-like members 5 are formed by injection molding of a soft resin such as a vinyl chloride resin.

As illustrated in FIG. 2A, the hub 3 is formed from a hub base portion 7 with the rear end connected to a flexible tube 6 and a small cylindrical portion 71 extending from the front end of the hub base portion 7 in the front-end direction. The rear end of the needle tube 2 is supported by the front end of the small cylindrical portion 71.

The hub 3 is formed by injection molding of a synthetic resin such as acrylonitrile-butadiene-styrene copolymer resin (ABS resin), for example.

Figure 2B:
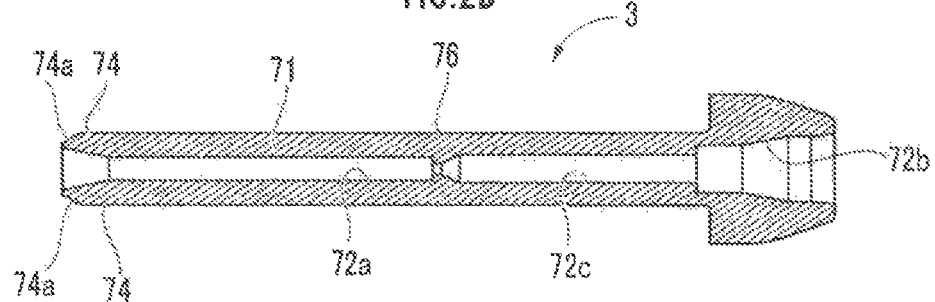
Figure 2C:
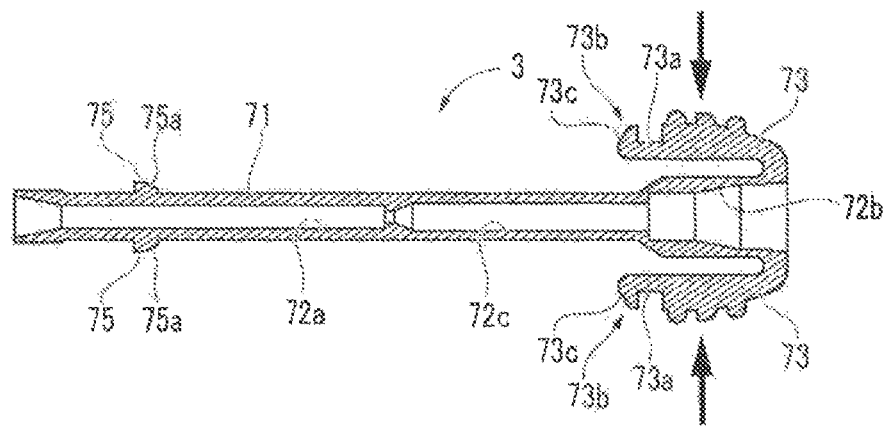

As illustrated in FIGS. 2B and 2C, the small cylindrical portion 71 includes a needle tube support portion 72a in which the needle tube 2 is inserted and supported at the front end side. The hub base portion 7 includes a connection tube portion 72b connected to the flexible tube 6 at the rear end side. The needle tube support portion 72a and the connection tube portion 72b communicate with each other via a hollow portion 72c in the middle thereof.

The rear end of the hub base portion 7 has a pair of arms 73 and 73 in symmetry with respect to the central axis of the small cylindrical portion 71 as illustrated in FIGS. 2A and 2C. The arms 73 and 73 are provided along the length of the small cylindrical portion 71 with a space from the hub base portion 7. Each of the arms 73 has a hook 73b via a neck portion 73a. The front end of the hook 73b has an inclination surface 73c from the front end side to the rear end side such that the side of the surface in proximity to the small cylindrical portion 71 is sharpened.

The hub base portion 7 is formed form an ABS resin as described above, and thus the arms 73 and 73 are pressurized in an arrow direction and are elastically deformable in the direction of the small cylindrical portion 71. When being depressurized, the arms 73 and 73 can return to the original state due to their elasticity.

As illustrated in FIGS. 2A to 2C, a first protrusion portion 74 and a second protrusion portion 75 are provided on the outer peripheral surface of the front end of the small cylindrical portion 71. The first protrusion portion 74 is provided on the front end of the small cylindrical portion 71, and the second protrusion portion 75 is provided closer to the rear end side than the first protrusion portion 74 with a first predetermined space from the first protrusion portion 74.

The first protrusion portions 74 protrude along a line orthogonal to a line connecting the arms 73 and 73 (corresponding to a first axial line of the present invention) as seen from the front end side. The second protrusion portions 75 protrude along the line connecting the arms 73 and 73 (corresponding to a second axial line of the present invention) as seen from the front end side.

A pair of first protrusion portions 74 is provided with a slope 74*a* at the front end in a vertically symmetrical manner (see FIG. 2A). The slopes 74*a* are formed to be gradually higher from the front end to the rear end. A pair of second protrusion portions 75 is provided with a slope 75*a* at the rear end in a horizontally symmetrical manner (see FIG. 2A). The slopes 75*a* are formed to be gradually lower from the front end to the rear end.

Streaks 76 are provided entirely on the outer peripheral surface of the small cylindrical portion 71 along the axial line from the first protrusion portions 74 to the hub base portion 7.

In the following description, the distance from the protrusion end of one first protrusion portion 74 to the protrusion end of the other first protrusion portion 74 will be called "height", and the maximum width in a direction orthogonal to both the height direction of the first protrusion portions 74 and the axial line of the small cylindrical portion 71. The foregoing definition also applies to the second protrusion portions 75.

In the foregoing embodiment, one each pair of the protrusion portions 74 and 75 is provided on the outer peripheral surface of the front end of the small cylindrical portion 71. Alternatively, one each of the protrusion portions 74 and 75 may be provided. In addition, the first protrusion portions 74 and the second protrusion portions 75 protrude with a phase shift of 90 degrees, but the present invention is not limited to this. The first protrusion portions 74 and the second protrusion portions 75 may have a phase shift of another degree as far as the first protrusion portions 74 and the second protrusion portions 75 do not protrude in parallel to each other (0 or 180 degrees).

Figure 3A:
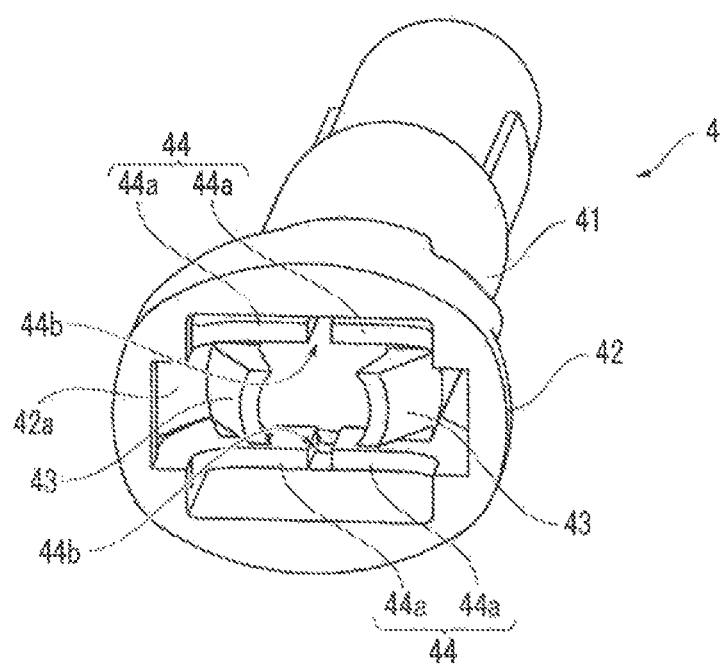
FIG. 3A, FIG. 3B and FIG. 3C are illustrative diagrams of a protector illustrated in FIG. 1.
Figure 3B:
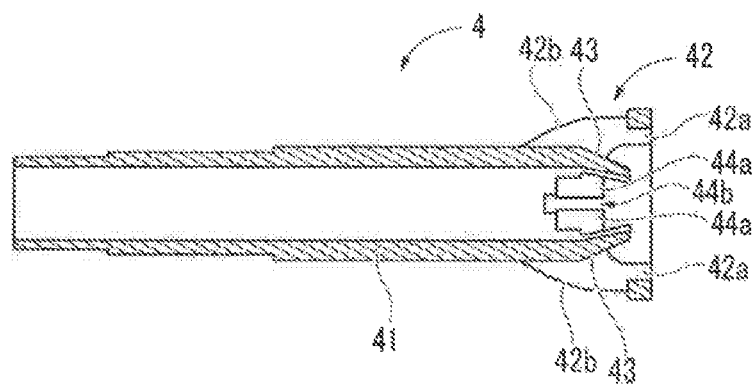
Figure 3C:
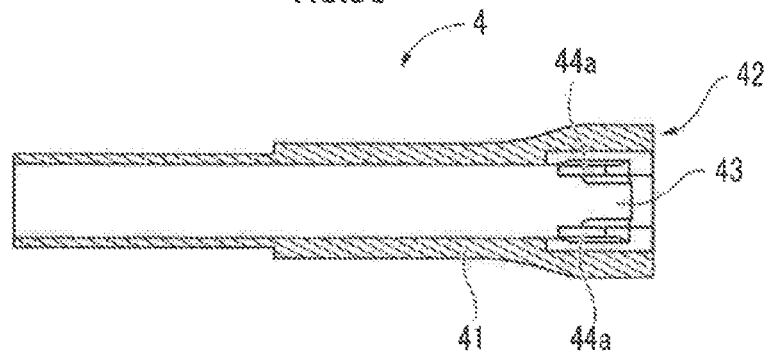

As illustrated in FIGS. 3A to 3C, the protector 4 includes a width-increased portion 42 that gradually increases in width from the front end side to the rear end side in a planar view (see FIG. 3B) at the rear end of a large cylindrical portion 41. The internal space in the large cylindrical portion 41 is set such that the small cylindrical portion 71 (including the protrusion portions 74 and 75) is slidable therein.

The rear end of the width-increased portion 42 includes insertion portions 42*a* and 42*a* into which the arms 73 and 73 are inserted. Each of the insertion portions 42*a* includes a window 42*b* on a lateral side such that the hook 73*b* of the arm 73 inserted into the insertion portion 42*a* is locked at the window 42*b*. That is, the arms 73 and the hooks 73*b* of the hub base portion 7 and the insertion portions 42*a* and windows 42*b* of the protector 4 constitute a first lock unit.

As illustrated in FIGS. 3A to 3C, the rear end of the protector 4 has protrusion pieces 43 and 43 and side wall portions 44 and 44.

As illustrated in FIGS. 3A and 3B, the protrusion pieces 43 and 43 are plate-like members that extend to the rear end side while inclining toward the axial line of the protector 4. A pair of protrusion pieces 43 and 43 is provided continuously from the rear end of the large cylindrical portion 41 in a horizontally symmetrical manner (see FIG. 3A). The lateral direction corresponds to a third axial line orthogonal to the axial line of the protector 4 in the present invention.

The protrusion pieces 43 are curved in a convex form outward from the axial line of the protector 4. The distance between the protrusion ends of the pair of protrusion pieces 43 and 43 is set to be equal to or longer than the height of the second protrusion portions 75 and 75. In the present embodiment, the distance between the protrusion ends of the pair of protrusion pieces 43 and 43 is set to be substantially equal to the diameter of the small cylindrical portion 71.

Since the protector 4 is formed from a polypropylene resin as described above, the protrusion pieces 43 are elastically deformable in the direction away from the axial line of the large cylindrical portion 41 (the horizontal direction illustrated in FIG. 3A).

The side wall portions 44 are provided with a second predetermined space from the front end side of the protrusion pieces 43 as illustrated in FIGS. 3A and 3B. The second predetermined space (the distance from the front ends of the side wall portions 44 to the rear ends of the protrusion pieces 43) is substantially identical to the first predetermined space (the distance from the rear ends of the first protrusion portions to the front ends of the second protrusion portions) in the present embodiment. However, the present invention is not limited to this but the second predetermined space may be equal to or smaller than the first predetermined space.

The side wall portions 44 are flat plate-like members that extend horizontally closer to the inner side than the inner peripheral surface of the large cylindrical portion 41 as illustrated in FIG. 3C. A pair of side wall portions 44 is provided in the vertical direction of the protrusion pieces 43. The vertical direction corresponds to a fourth axial line that crosses the third axial line at a predetermined angle as seen from the axial line of the protector in the present invention.

The distance between the pair of side wall portions 44 and 44 is equal to or longer than the width of the protrusion portions 74 and 75, and is equal to or shorter than the height of the protrusion portions 74 and 75. In the present embodiment, the distance between the pair of side wall portions 44 and 44 is set to be substantially equal to the diameter of the small cylindrical portion 71.

Each of the side wall portions 44 is formed from a pair of plate spring members 44*a* and 44*a*. The plate spring members 44*a* extend from the inner peripheral surface of the large cylindrical portion 41 toward the center along the horizontal direction. In addition, there is a space provided between the plate spring members 44*a* and the inner peripheral surface of the large cylindrical portion 41 (the width-increased portion 42). The protector 4 is formed from a polypropylene resin as described above and thus the plate spring members 44*a* are elastically deformable outward of the large cylindrical portion 41 (the vertical direction illustrated in FIG. 3A). The protrusion ends of the pair of plate spring members 44*a* and 44*a* constituting each of the side wall portions 44 have a slit 44*b* formed by a predetermined space therebetween.

In the present embodiment, the slits 44*b* are formed by the pairs of plate spring members 44*a*, but the present invention is not limited to this. The slits 44*b* may be formed by making grooves in the side wall portions 44.

Next, an operation of storing the needle tube 2 into the protector 4 in the medical needle with a protector 1 after removal from a blood vessel or the like will be described with reference to FIGS. 4A, 4B and 5.

Figure 4A:
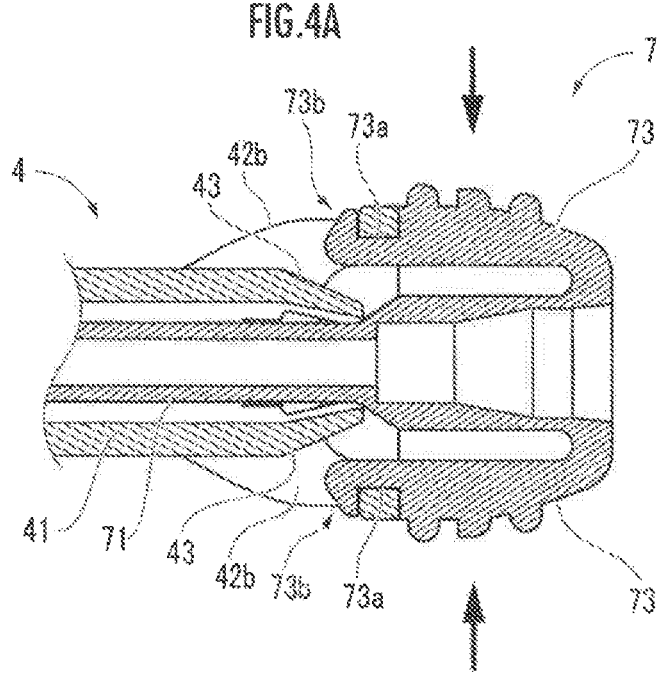
FIG. 4A is a horizontal cross-sectional view of main components of the hub assembled into the protector.

When the needle tube 2 is inserted into a blood vessel or the like, as illustrated in FIG. 4A, the hooks 73*b* at the front ends of the arms 73 in the hub base portion 7 are locked in the windows 42b of the protector 4 so that the needle tube 2 is protruded from the protector 4.

Accordingly, after the removal of the needle tube 2 from the blood vessel or the like, the arms 73 are pressurized in the direction of arrow and are elastically deformed in the direction of the small cylindrical portion 71 to unlock the hooks 73b from the windows 42b.

Figure 4B:
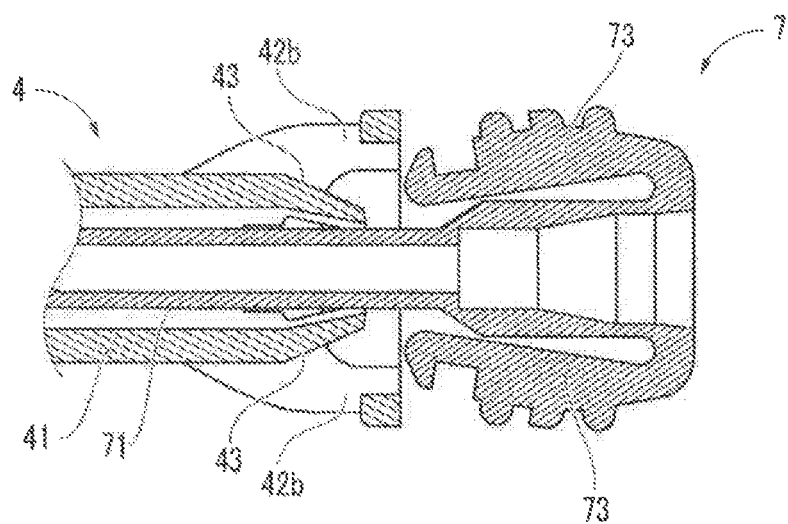
FIG. 4B is a horizontal cross-sectional view of main components of the hub unlocked from the protector.

Then, as illustrated in FIG. 4B, the hub 3 is moved backward while the arms 73 remain deformed in the direction of the small cylindrical portion 71. Accordingly, the needle tube 2 is drawn into the large cylindrical portion 41. At this time, as illustrated in FIG. 7C, the streaks 76 of the small cylindrical portion 71 are guided by the slits 44b and thus the hub 3 can be smoothly moved backward.

Figure 5A:
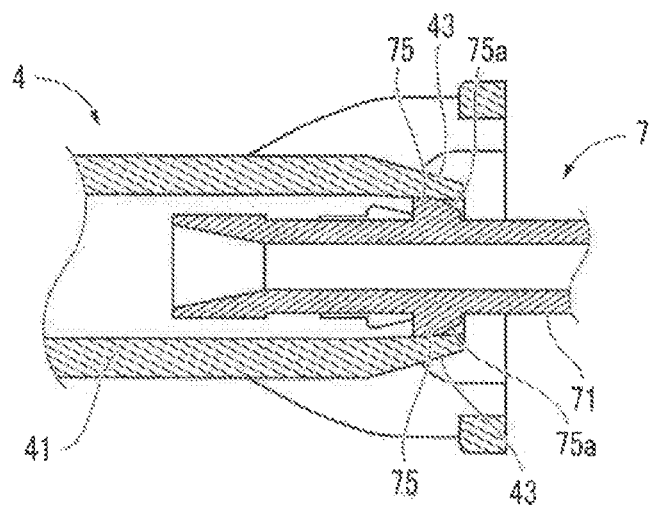
FIG. 5A is a horizontal cross-sectional view of the hub being moved backward.

Then, when the hub 3 is moved backward, the second protrusion portions 75 and 75 abut with the protrusion pieces 43 and 43 as illustrated in FIG. 5A. The protrusion pieces 43 are elastically deformable as described above, and thus are guided by the slopes 75a of the second protrusion portions 75 in the direction away from the axial line of the large cylindrical portion 41 (the vertical direction illustrated in FIG. 5A).

Figure 5B:
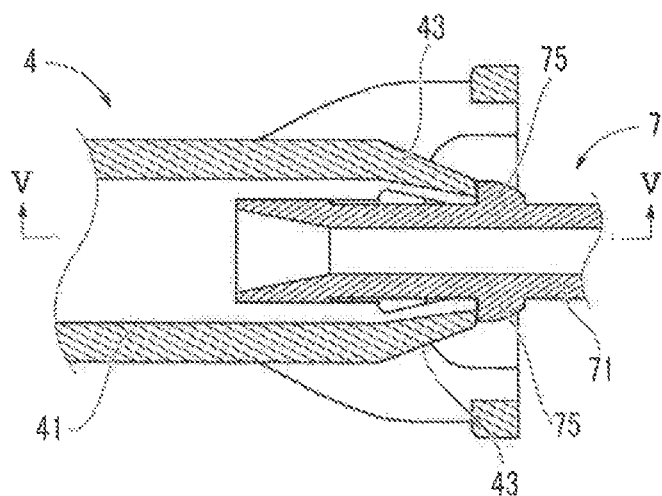
FIG. 5B is a horizontal cross-sectional view of the hub completely moved backward.

After that, as illustrated in FIG. 5B, when the hub 3 is further moved backward and the needle tube 2 not illustrated in the drawing is stored in the large cylindrical portion 41, the protrusion pieces 43 and 43 go over the second protrusion portions 75 and 75 and return to the original state by their elasticity. Then, the protrusion pieces 43 and 43 are fitted into clearances between the first protrusion portions 74 and the second protrusion portions 75. Accordingly, in a planar view (see FIG. 5B), the rear ends of the protrusion pieces 43 and 43 are locked by the front ends of the second protrusion portions 75 and 75.

Figure 5C:
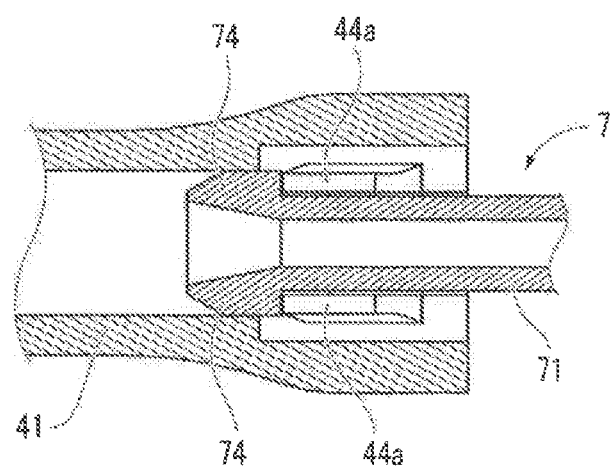
FIG. 5C is a cross-sectional view of FIG. 5B taken along line V-V.

At this time, the distance from the front ends of the side wall portions 44 to the rear ends of the protrusion pieces 43 (second predetermined distance) is substantially identical to the distance from the rear ends of the first protrusion portions to the front ends of the second protrusion portions (first predetermined space) as described above, the front ends of the side wall portions 44 are also locked by the rear ends of the first protrusion portions 74 and 74 in a side view (see FIG. 5C).

That is, the protrusion pieces 43 and the side wall portions 44 of the protector 4 are sandwiched between the protrusion portions 74 and 75 of the hub 3. In the present embodiment, the protrusion portions 74 and 75 of the hub 3 and the protrusion pieces 43 and the side wall portions 44 of the protector 4 constitute a second lock unit of the present invention.

As a result, the protrusion pieces 43, the side wall portions 44, and the protrusion portions 74 and 75 cannot be unlocked unless the protrusion pieces 43 are deformed outward, and thus the needle tube 2 will not be protruded again from the large cylindrical portion 41. This makes it possible to prevent wrong insertion.

Next, the operation of assembling together the separately molded hub 3 and protector 4 will be described with reference to FIGS. 6A to 6D.

To assemble the hub 3 into the protector 4, the front end side of the hub 3 is inserted into the rear end side of the protector 4. At this time, if an attempt is made to insert the front end side of the hub base portion 7 into the rear end side of the protector 4 in such a manner as to insert the pair of arms 73 and 73 of the hub base portion 7 into the insertion portion 42a of the large cylindrical portion 41, the space between the protrusion ends of the pair of protrusion pieces 43 and 43 is equal to or shorter than the height of the second protrusion portions 75 and 75 and thus the front ends of the second protrusion portions 75 and 75 hit against the protrusion ends (rear ends) of the protrusion pieces 43 and 43.

Figure 6A:
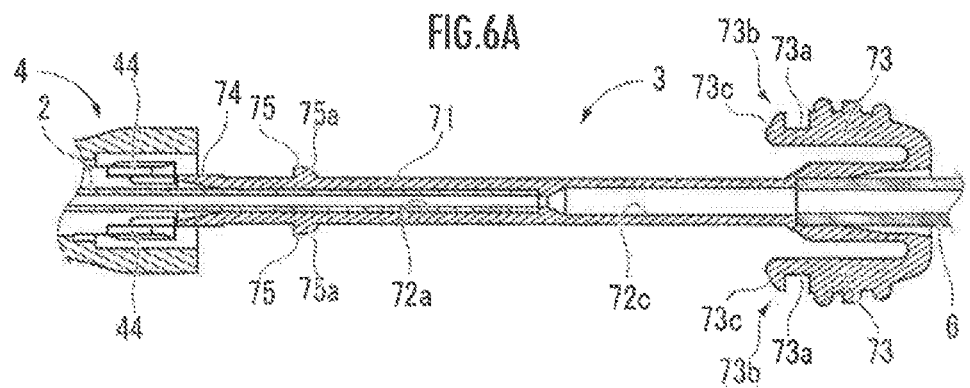
FIG. 6A is a vertical cross-sectional view of the protector and the hub relatively 90° rotated around their central axes.

Accordingly, as illustrated in FIG. 6A, the protector 4 and the hub 3 are relatively rotated 90° around their central axes. Then, when an attempt is made to insert the front end side of the hub 3 into the rear end side of the protector 4, the protrusion pieces 43 are elastically deformable as described above, and thus the protrusion pieces 43 are guided along the slopes 74a of the first protrusion portions 74 and deformed in the direction away from the axial line of the large cylindrical portion 41, and then the first protrusion portions 74 and 74 pass through the protrusion pieces 43 and 43 and move toward the front end side.

Further, as illustrated in FIG. 6A, when the pair of side wall portions 44 and 44 is oriented in the vertical direction, the width direction of the first protrusion portions 74 is aligned with the vertical direction. The distance between the pair of side wall portions 44 and 44 is set to be equal to or longer than the width of the first protrusion portions 74, and thus the first protrusion portions 74 pass through the side wall portions 44 and 44.

In addition, the second protrusion portions 75 and 75 are relatively rotated 90° around the central axes, which makes it possible to prevent a collision with the protrusion pieces 43.

Figure 6B:
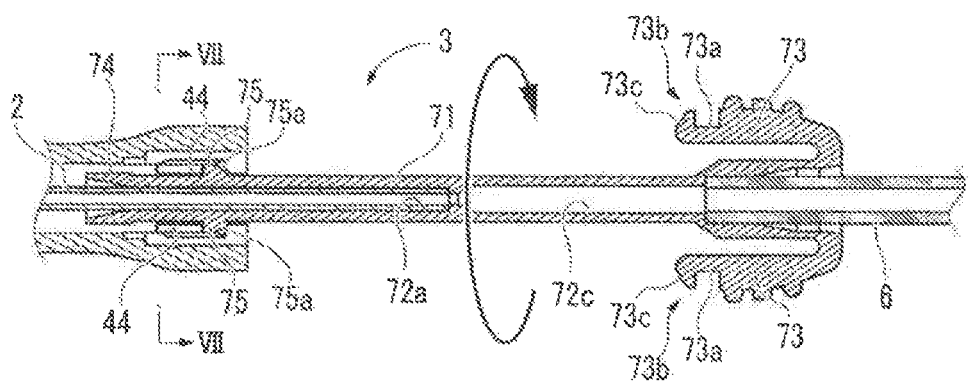
FIG. 6B is a vertical cross-sectional view of the state in which a front end side of the hub is inserted into a rear end side of the protector.

Then, when the hub 3 is moved forward, the second protrusion portions 75 and 75 hit against the side wall portions 44 and 44 as illustrated in FIG. 6B.

Next, as indicated with an arrow in FIG. 6B, the protector 4 and the hub 3 are relatively rotated 90° in the direction opposite to the former direction around their central axes. Accordingly, the hub 3 returns into the position where the arms 73 and 73 can be inserted into the insertion portions 42a and 42a of the protector 4.

The state of deformation of the side wall portions 44 by the streaks 76 at this time will be described with reference to FIGS. 7A to 7C.

First, FIG. 7A is a cross-sectional view of FIG. 6B taken along line VII-VII. When the plate spring members 44a and 44a in this state are rotated in the direction of arrow, the plate spring members 44a and 44a are elastically deformable with respective vertical spaces and thus are pushed into the streaks 76 and 76 and deformed in the direction away from the axial line of the large cylindrical portion 41 as illustrated in FIG. 7B.

When the plate spring members 44a and 44a are rotated in the direction of arrow, the plate spring members 44a and 44a go over the streaks 76 and 76 and return to the original state due to their elasticity as illustrated in FIG. 7C. Accordingly, the streaks 76 and 76 are fitted into the slits 44b between the pairs of opposed plate spring members 44a and 44a.

Returning to FIGS. 6A to 6D, the operation after the completion of the rotation will be described. At this time, the first protrusion portions 74 and 74 have already passed through the side wall portions 44 and 44 and thus the first protrusion portions 74 and 74 are arranged closer to the front end side than the side wall portions 44 as illustrated in FIG. 6C.

In addition, the second protrusion portions 75 and 75 are rotated in the state of having moved forward closer to the front end side than the protrusion ends of the protrusion pieces 43 and 43. Accordingly, as illustrated in FIG. 6D, the second protrusion portions 75 and 75 are arranged closer to the front end side than the protrusion ends (rear ends) of the protrusion pieces 43 and 43 while forcedly opening the protrusion pieces 43 and 43.

Figure 6C:
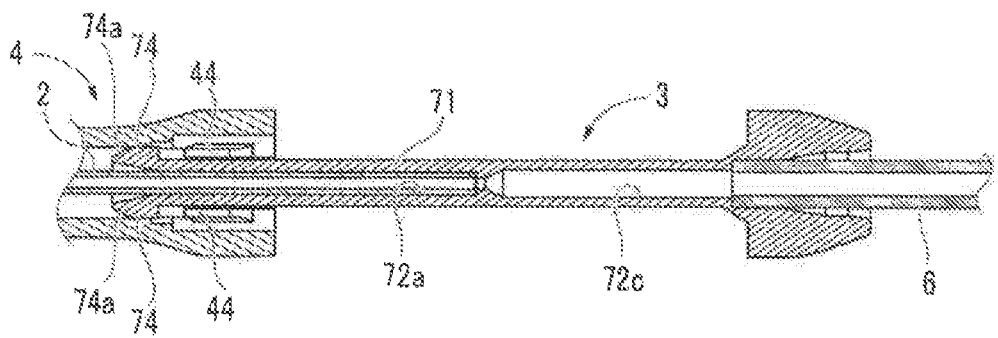
FIG. 6C is a vertical cross-sectional view of the state in which the protector and the hub are relatively rotated 90° in opposite directions around their central axes.
Figure 6D:
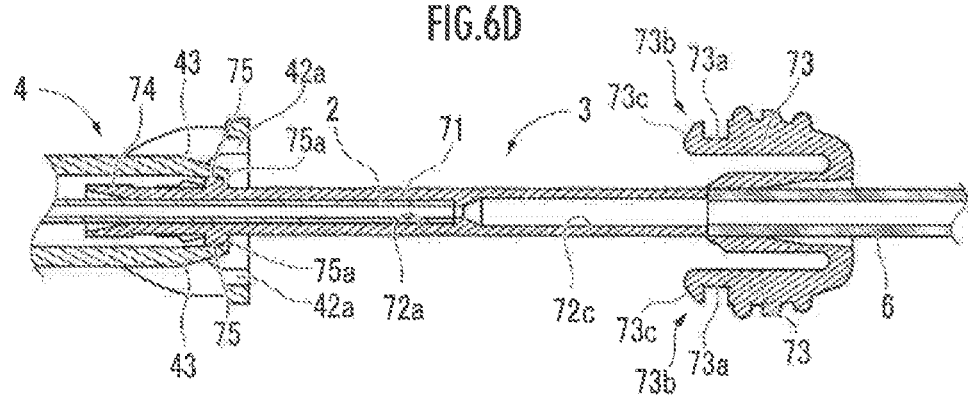
FIG. 6D is a horizontal cross-sectional view of FIG. 6C.

Accordingly, while the hub 3 is moved forward, when the pair of side wall portions 44 and 44 is oriented in the vertical direction, the width direction of the second protrusion portions 75 is aligned with the vertical direction as illustrated in FIG. 6C. The distance between the pair of side wall portions 44 and 44 is set to be equal to or longer than the width of the second protrusion portions 75, and thus the second protrusion portions 75 also pass through the side wall portions 44 and 44.

When the hub 3 is further moved forward and the arms 73 collide with the insertion portions 42a, the arms 73 have inclined surfaces 73c at front ends and thus are gradually pressurized and deformed toward the small cylindrical portion 71 and inserted into the insertion portions 42a. When the hub 3 is further moved forward in that state, the hooks 73b at the front ends of the arms 73 reach the windows 42b and the arms 73 are released from the pressure. Accordingly, the arms 73 return to the original state due to their elasticity and the hooks 73b are locked in the windows 42b.

As a result, as illustrated in FIG. 4A, the hub 3 can be assembled into the protector 4.

Next, a medical needle with a protector according to a modification example of the present embodiment will be described with reference to FIGS. 8A to 8C.

Figure 8A:
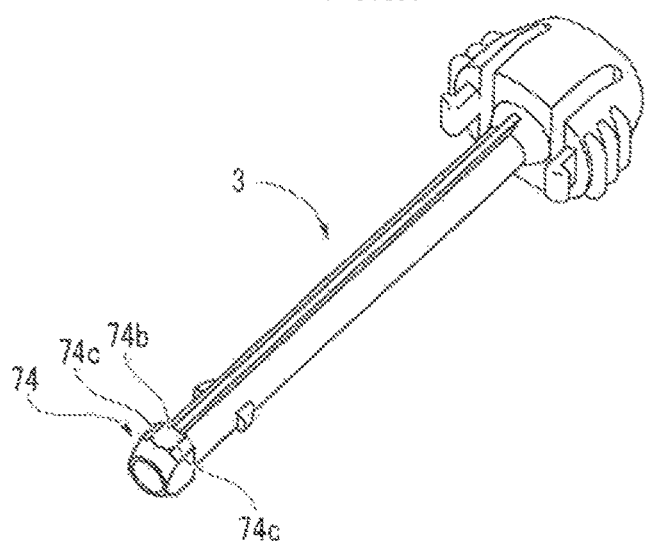
FIGS. 8A, 8B and 8C are illustrative diagrams of a modification example of the medical needle with a protector according to the embodiment.

A hub 3 according to the modification example further has a first flat surface 74b on part of the outer peripheral surface of the first protrusion portion 74 in the vertical direction (see FIG. 8A) as illustrated in FIG. 8A. The first flat surface 74b connects to other outer peripheral surfaces of the first protrusion portion 74 via step portions 74c.

Figure 8B:
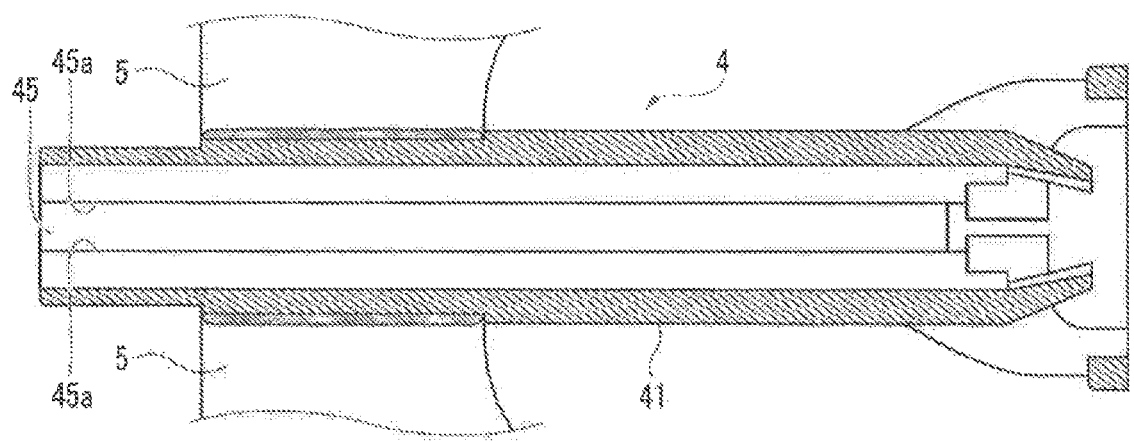

In addition, the inner peripheral surface of a protector 4 according to the modification example has a second flat portion 45 corresponding to the first flat portion 74b along the axial line of the protector 4 from the front end to rear end as illustrated in FIG. 8B. The second flat portions 45 are vertically provided on the inner peripheral surface of the large cylindrical portion 41 and connect to other inner peripheral surfaces of the large cylindrical portion 41 via step portions 45a corresponding to the step portions 74c.

Figure 8C:
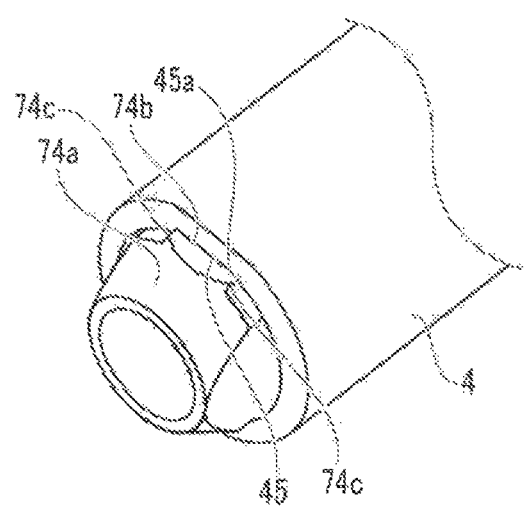

Accordingly, as illustrated in FIG. 8C, the flat surface 74b of the hub 3 and the flat surface 45 of the protector 4 slide on each other with the step portions 74c and 74c of the hub base portion 7 sandwiched between the step portions 45a and 45a of the protector 4. Therefore, according to the medical needle with a protector in the modification example, the hub 3 can be moved backward more smoothly.

REFERENCE SIGNS LIST

1 Medical needle with a protector
2 Needle tube
3 Hub
4 Protector
Wing-like portion
6 Flexible tube
41 Large cylindrical portion
42 Width-increased portion
42a Insertion portion (first lock unit)
42b Window (first lock unit)
43 Protrusion piece (second lock unit)
72a Needle tube support portion
72b Connection tube portion
72c Hollow portion
73 Arm (first lock unit)
75 Second protrusion portion (second lock unit)

The invention claimed is:

1. A medical needle with a protector comprising:
a hub at a front end supporting a rear end of a needle tube;
a cylindrical protector that is capable of storing the needle tube by sliding the hub;
a first lock unit that locks the hub to the protector in a manner capable of unlocking in a first state that the needle tube is protruded from the protector; and
a second lock unit that locks the hub to the protector in a manner incapable of at least a transition to the first state and in a second state that the needle tube is stored in the protector, wherein
a front end side part of the hub includes a protrusion portion that forms an end surface facing to the front end side and extending from an outer peripheral surface of the hub in a direction away from a longitudinal axial line of the hub,
the protector includes:
a large cylindrical portion extending in a direction of a longitudinal axis line of the protector;
a protrusion piece that is provided on a rear end side of the large cylindrical portion, extends to a rear end side of the protector, and is elastically deformable in a direction away from the longitudinal axis line of the protector; and
a width-increased portion that is provided on an outer peripheral side of the protrusion piece on the rear end side of the large cylindrical portion, has a larger diameter than the large cylindrical portion, and has a minor axis and a major axis when viewed along the direction of the longitudinal axis line of the protector,
the second lock unit is configured such that, a rear end side of the protrusion piece contacts with the end surface of the protrusion portion in the second state, and
the protrusion piece is formed integrally with the large cylindrical portion on the major axis side of the width-increased portion.

2. The medical needle with the protector according to claim 1, wherein
the protrusion piece has a surface inclined to the longitudinal axis line of the protector on a side of the longitudinal axis line of the protector.

3. The medical needle with the protector according to claim 1, wherein
the first lock unit is configured such that, a window provided on the major axis side of the width-increased portion is locked to the hub, and
the window is provided to open the outer peripheral side of at least a part of the protrusion piece.

4. The medical needle with the protector according to claim 1, wherein
the hub includes a connection tube portion connected to a flexible tube,
the first lock unit is configured such that, a window provided on the major axis side of the width-increased portion is locked to an arm provided on the hub, and
at least a part of the connection tube portion is located on a rear end side from a rear end of a part along a length of the hub with a space from the arm.

5. The medical needle with the protector according to claim 1, wherein
the protector includes a recessed portion provided on the minor axis side of the width-increased portion.

6. The medical needle with the protector according to claim 1, wherein the hub includes:
a needle tube support portion supporting the needle tube;
a connection tube portion connected to a flexible tube; and
a hollow portion connecting the needle tube support portion and the connection tube portion.

7. The medical needle with the protector according to claim 1, wherein
the protector has a wing-like member extending to the major axis side of the width-increased portion.

* * * * *